(12) United States Patent
Ruckdeschel et al.

(10) Patent No.: US 7,219,664 B2
(45) Date of Patent: May 22, 2007

(54) BREATH ACTUATED INHALER

(75) Inventors: Tom Ruckdeschel, Apex, NC (US);
Perry Genova, Chapel Hill, NC (US);
Dan Deaton, Apex, NC (US); Matt Khare, Willow Springs, NC (US)

(73) Assignee: Kos Life Sciences, Inc., Weston, FL (US)

( * ) Notice: Subject to any disclaimer, the term of this patent is extended or adjusted under 35 U.S.C. 154(b) by 27 days.

(21) Appl. No.: 10/908,133

(22) Filed: Apr. 28, 2005

(65) Prior Publication Data
US 2006/0243275 A1 Nov. 2, 2006

(51) Int. Cl.
*A61M 11/00* (2006.01)
(52) U.S. Cl. .................... 128/200.14; 128/200.23; 239/463
(58) Field of Classification Search ................
128/200.21–200.24, 203.12, 203.14, 203.15,
128/203.19, 203.24, 203.28, 205.15, 205.16,
128/205.23, 200.16, 200.17, 203.21, 200.14;
239/463, 466, 474, 491; 604/58
See application file for complete search history.

(56) References Cited

U.S. PATENT DOCUMENTS

| 5,020,527 | A | * | 6/1991 | Dessertine | 128/200.23 |
| 5,447,150 | A | * | 9/1995 | Bacon | 128/200.14 |
| 6,418,925 | B1 | * | 7/2002 | Genova et al. | 128/200.14 |

OTHER PUBLICATIONS

WO 93/24167, Holroyd, M. et al. Dose Indicating Device, Dec. 9, 1993, 23 pages.*

* cited by examiner

*Primary Examiner*—Justine R. Yu
*Assistant Examiner*—Shumaya Ali
(74) *Attorney, Agent, or Firm*—Karen P. Bechtold, Esq.; Jonathan N. Provocot, Esq.

(57) ABSTRACT

A breath actuated metered dose inhaler including a housing, a mouthpiece positioned at one end of the housing, and a mechanical release mechanism positioned at another end of the housing. The release mechanism is triggered by a diaphragm and the inhaler is configured such that the air inhalation pathway is unimpeded by the release mechanism.

16 Claims, 10 Drawing Sheets

BREATH ACTUATED INHALER

FIELD OF THE INVENTION

The present invention is directed to a breath actuated pulmonary drug delivery device used in the delivery of fluid dispensations from a drug-containing canister. The delivery device provides a metered dose of drug or other therapeutic agent when the patient inhales from the device.

DESCRIPTION OF THE PRIOR ART

There are a variety of inhalation devices which release aerosol medication, either in a continuous spray or in a predetermined amount of medication, commonly referred to as a metered dose. Most common in this category are "press and breathe", canister in actuator, delivery systems (pMDIs or pressurized metered dose inhalers). In these devices, drug for multiple doses is stored under pressure in a canister fitted at one end with a metering valve and an associated discharge port or stem. When inserted into an actuator body with mouthpiece, a "puff" or single dose of the stored drug is metered and delivered when the patient depresses the canister within the actuator. The spray is applied directly into the patient's mouth, nasal area or respiratory airways. Typically, these devices are actuated by the pressure applied by the user's fingers, button action, or other related manual techniques.

Proper use of these manually actuated devices requires that the spray be activated at the appropriate point in the inspiratory cycle, so that the medication is carried into the lungs rather than being deposited in the mouth or throat. If this actuation is not correctly coordinated with the inspiratory phase, the metered dose may be deposited differently with each actuation and potentially compromise the therapeutics and safety of the product.

There are numerous factors leading to poor coordination of actuation of the spray and the inspiration cycle. Included in those factors are poor training, the inherent limitations of the users (if any), such as impaired physical abilities of geriatric patients or the as-yet-undeveloped skills of children, or their inability of either group to comprehend the correct way to use the device. In view of the difficulties associated with manually actuated devices, it has been recognized that there is a need for correct and accurately delivered doses for patients having either local or systemic pulmonary diseases. It has been further recognized that a reliable breath activated device would improve the quality of life for these afflicted people.

A breath actuated inhaler helps eliminate the problems associated with manually actuated inhalers by making the product easier to coordinate and more patient friendly, with predictable delivery and dispersion in the respiratory airways. Breath-actuated inhalers (U.S. Pat. Nos. 5,408,994 and 5,447,150) address the problems associated with synchronization of drug delivery with inhalation. Both commercially available devices, however, rely on either pneumatic or mechanical functions that generally limit their utility. Further, they do not incorporate added features of importance to patients, i.e. low spray velocity and indication of number of drug doses or "puffs" remaining after each use.

SUMMARY OF THE INVENTION

The inventors have recognized that while there are metered dose inhalation devices that are activated by the breath of users, a greatly improved breath actuated device could be developed. The present invention is directed toward a breath actuated metered dose inhaler that overcomes many of the drawbacks associated with prior inhalers.

A breath actuated metered dose inhaler according to the invention includes a housing, a mouthpiece positioned at one end of the housing, and a mechanical release mechanism positioned at another end of the housing. The release mechanism is triggered by a diaphragm and the inhaler is configured such that the air inhalation pathway is unimpeded by the release mechanism.

The velocity, with which the inhaler discharges drug and propellant, is extremely important. If too high drug particles may impact upon the throat inducing a gagging or choking reflex thus limiting the amount of drug reaching the lung. It is also important that the actuator nozzle delivering the plume provide aerosolization and deaggregation of drug in suspension to insure particle sizes appropriate for delivery to the desired target area within the lung. The device of the present invention may employ a nozzle of conventional design. A preferred embodiment, however, might utilize a vortex nozzle as described in U.S. Pat. No. 6,418,925, which is commonly assigned and the contents of which are expressly incorporated herein by reference, producing a slowly moving spray while meeting aerosolization requirements with less retention of drug within the structure.

An additional feature of the invention, herein, is the inclusion of a record keeping means as described in U.S. Pat. Nos. 5,544,647 and 5,622,163, which are commonly assigned and the contents of which are expressly incorporated herein by reference. An electronic event counter provides the patient with a numerical indication of puffs remaining in the canister as well as the number of puffs taken in a sequence to obtain a prescribed dose. This information display assures that the patient can be kept aware of depletion of medication in time to refill their prescription. This breath-actuated inhaler overcomes deficiencies apparent in earlier mechanical and pneumatic devices while adding additional user benefits. A breath-actuated metered dose inhaler according to the invention is housed within a structure in a form to comfortably fit in the hand of the user. Said housing includes a mouthpiece positioned at one end and a mechanical release mechanism at another end. A diaphragm in the inhalation air passageway triggers the release mechanism. Inclusion of an event counter and a vortex drug delivery nozzle are facilitated by the design of the structure.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which:

FIG. 1 is an external view of one embodiment of the compact, hand held, breath-actuated inhaler;

FIG. 2 is a rotated, perspective view, of the breath-actuated inhaler of FIG. 1 showing the location of an electronic event counter not visible in FIG. 1;

FIG. 3 is a plan view of the mechanism of the breath-actuated inhaler of FIG. 1 in the initial armed, at rest, state;

FIG. 4 is a plan view of the mechanism of the breath-actuated inhaler of FIG. 1 in the mouthpiece cover open, armed, cocked and ready to fire state.

FIG. 5 is a plan view of the mechanism of the breath-actuated inhaler of FIG. 1 in the actuated state;

DETAILED DESCRIPTION OF THE PREFERRED EMBODIMENTS

The breath actuated inhaler of the present invention is suitable for the delivery of practically any inhaled aerosol medication that would benefit from the controlled, precision delivery offered by a breath actuated inhaler.

Prior to discussing the advantages of the present breath actuated inhaler, the structure and function of the inhaler will be described.

The device of the invention can generally be made using parts molded of plastic materials, with the exception of springs, generally made of metal and seals, gaskets and diaphragms made of elastomeric materials. Components of the electronic event counter may include semiconductor elements, battery, circuit board and display means.

Figure 1:
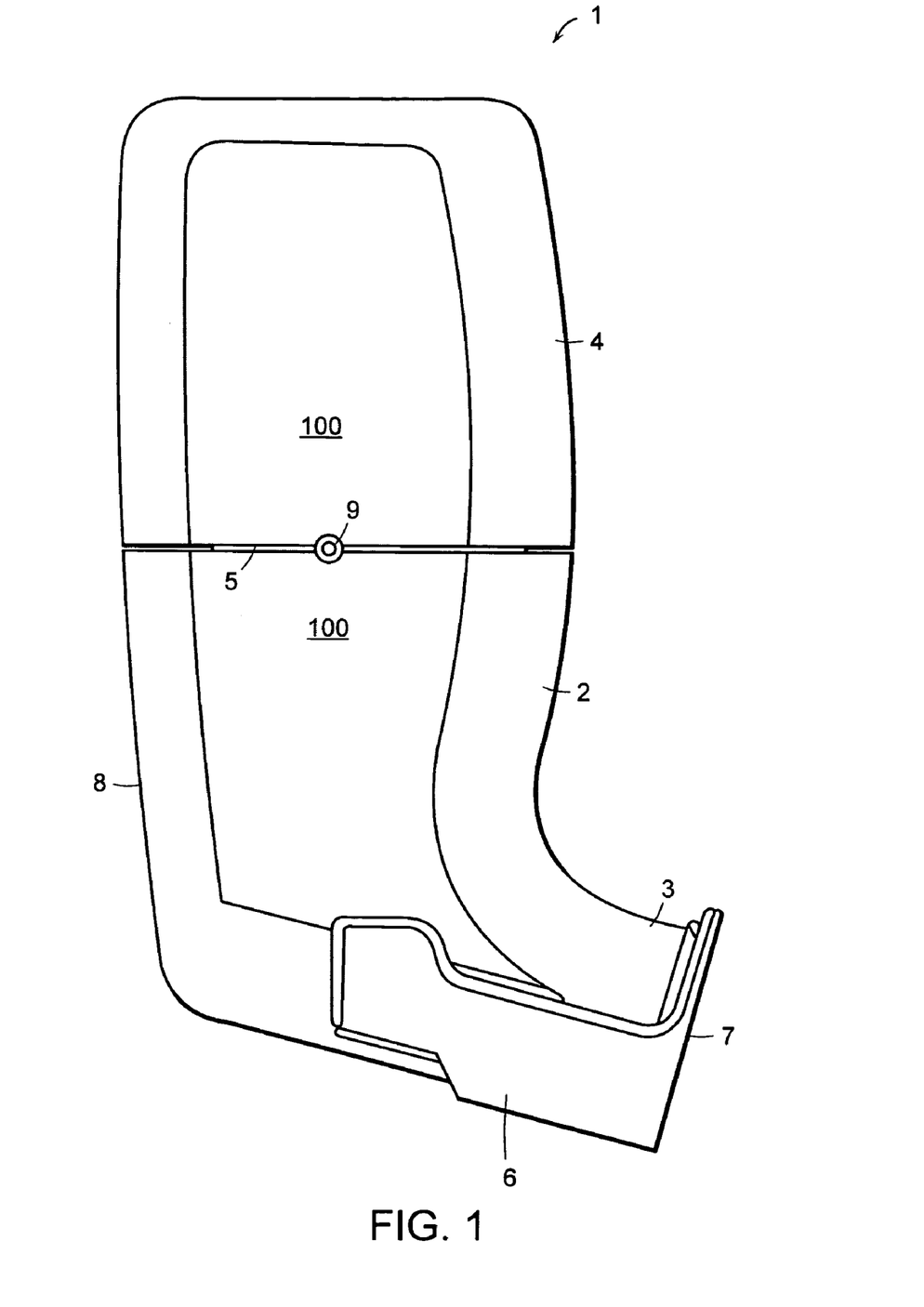

FIG. 1 depicts an external view of the hand held, breath-actuated inhaler 1 according to the present invention. The housing structure 100 consists of a lower section 2 with a mouthpiece 3, and an upper section 4. A bayonet type twist lock at mid portion 5 joins the lower section 2 and the upper section of the housing structure 100.

Figure 2:
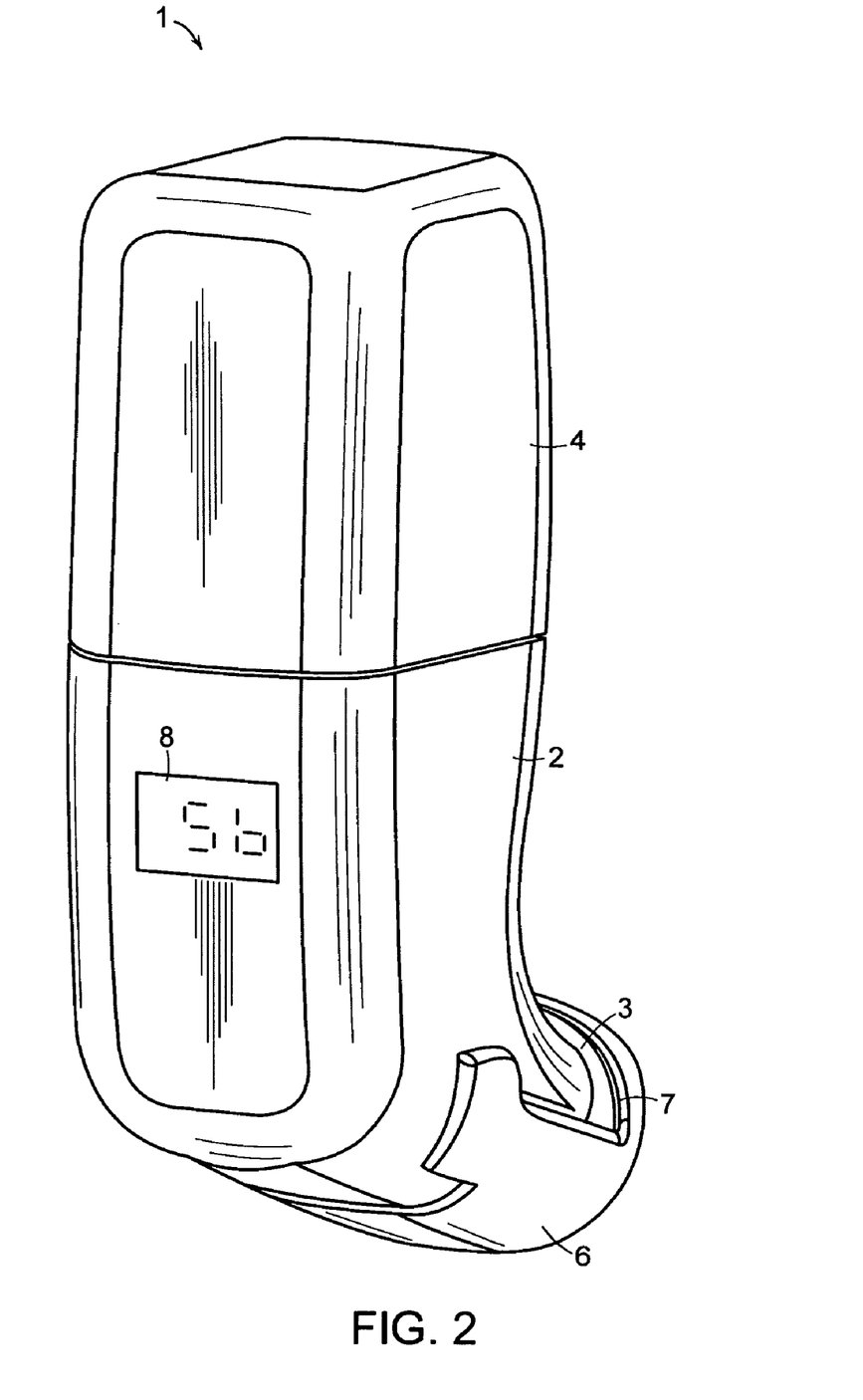

Pivotally attached to lower section 2 is a cocking lever 6 which may have an integral mouthpiece cover 7. Not visible in this view but located on the back of the inhaler 1 in lower section 2 is a window for viewing the numerical display of event counter 8 (described in more detail below). Between lower section 2 and upper section 4 is included a vent port 9 for inspiratory "make up" air. In FIG. 2, the breath-actuated inhaler 1 is rotated so as to show the position of event counter 8 in the back of lower section 2.

Figure 3:
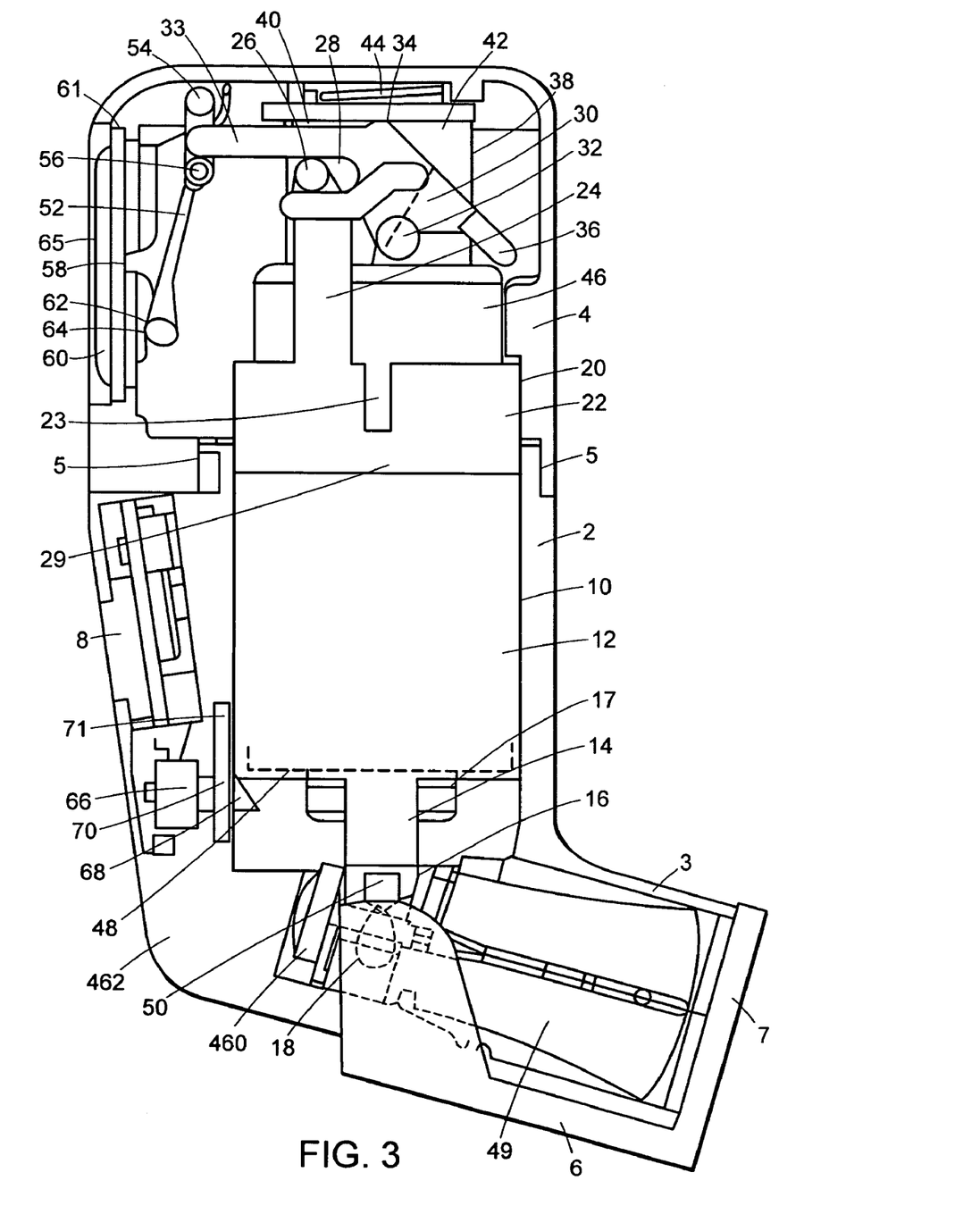

FIG. 3 is a plan view of the mechanism within the housing structure 100 of FIG. 1 in the initial, armed, at rest, state. Lower section 2 of housing structure 100 has a cylindrical cavity 10 in which a sleeve 12 (shown in detail in FIG. 7) is fitted. Projecting from the lower end 17 of sleeve 12 are two posts 14 that are displaced 180-degrees apart. Posts 14 extend through openings 16 in the bottom of lower section 2 and bear upon cam lobes 18 (shown by dotted line) on the inside of cocking lever 6 (shown in detail in FIG. 6). Lower and upper sections 2, 4 are joined by means of a bayonet twist lock 5. A cylindrical cavity 20 in upper section 4 of housing structure 100 retains sliding load sleeve 22 (shown in detail in FIG. 8), the lower end 29 of which is in contact with the upper edge 27 of sleeve 12 (see FIG. 7). A slot 23 in the upper edge of the sliding load sleeve 22 is an element of a shuttle valve for the ingress of ambient air post drug delivery (makeup air) to insure an uninhibited continuation of the inhalation maneuver.

Figure 12:
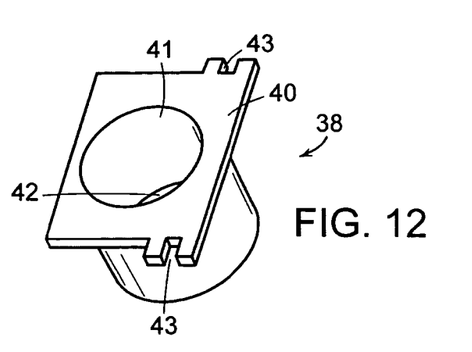
FIG. 12 is a perspective view of the spring cup positioned between main the spring and the drug canister.

The upper end of load sleeve 22 has two projecting arms 24, which at their upper extremity have cylindrical bosses 26 set at right angles to the projecting arms 24. Cylindrical bosses 26 engage receiver slot 28 in toggle 30. The top radius of the cylindrical bosses 26 bear against the lower surface of platen 33 to oppose the force of main spring 44. Toggle 30 rotates on integral axle 32, the ends of which are seated within bearing sockets molded into upper section 4 of housing structure 100. The features of toggle 30 are best understood by the study of FIG. 9. A platen 33 on toggle 30 has projecting nodes 34 at a junction with shelf 36. The center section of toggle 30 is cut away at 35 to allow for passage there through of spring cup 38 that is depicted in FIG. 12. Upper end 40 of spring cup 38 is a platform which projects out from spring clamp 38, where upon the under side of platform end 40 bears nodes 34 of toggle 30. Interior floor 42 forms a seat in the cylindrical portion 41 of spring cup 38 for main spring 44, which is held captive between 42 and the inner, top, surface of upper section 4 of housing structure 100.

A pressurized metered dose inhaler (PMDI) canister 46 rides within sleeve 12 and load sleeve 22. The lower end of spring cup 38 rests against the bottom of the PMDI canister 46. Canister 46 has, at the other end, a ferrule 48 retaining a metering valve therein which discharges a discrete dose of drug upon displacement of a delivery stem 50. Delivery stem 50 engages vortex nozzle 49 (described in more detail below) within mouthpiece 3. The twist lock feature 5 facilitates separation of upper and lower sections 2, 4 in order to access PMDI canister 46 for priming and vortex nozzle 49 for cleaning. Additionally, accessing PMDI canister 46 allows a user to manually operate the inhaler 1 by pressing down on the canister 46 in order to manually operate the device in the event of a failure of the actuating mechanism.

Figure 9:
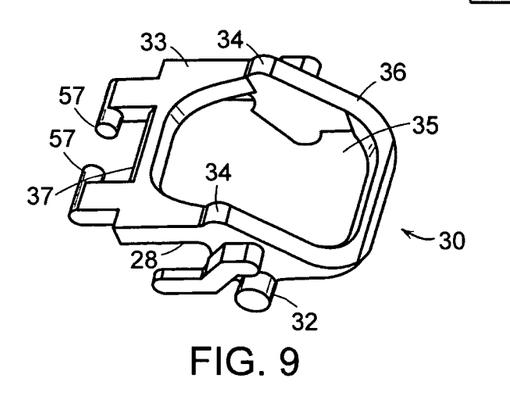
FIG. 9 is a perspective view of the toggle showing details of the functional elements.
Figure 10:
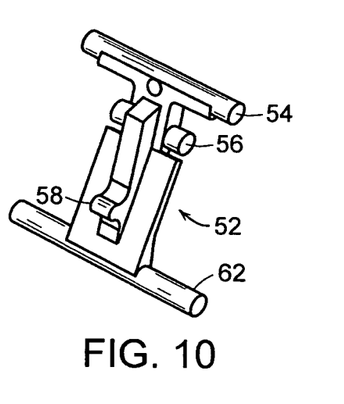
FIG. 10 is a perspective view of the escapement that releases the toggle upon initiation of an inhalation maneuver.
Figure 13:
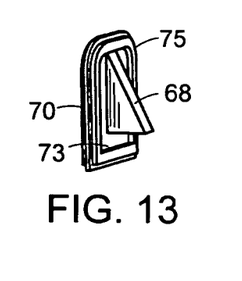
FIG. 13 is a perspective view of the membrane event counter switch trigger.

An escapement 52 as shown in FIG. 10, pivots about post 54, which is retained by bearings molded in upper section 4 of housing structure 100. Rollers or rounded, low friction surfaces, 56 on escapement 52 support cylindrical bars 57 projecting from the distal inner end of platen 33 of toggle 30 when the inhaler is armed and cocked. As depicted in FIG. 9, an opening 37 is provided in toggle 30 to permit rollers 56 to pass through upon displacement of escapement 52. A finger 58 projecting from the face of escapement 52 contacts the center 59 of elastomeric diaphragm 60 shown in FIG. 11. Elastomeric diaphragm 60 is retained within a channel 61 that is molded into upper section 4. Rail 62 at the bottom edge of escapement 52 rests on stop 64 in upper section 4 in order to accurately set the angular position of the escapement 52. Mounted within lower section 2 is an electronic event counter 8. Count recordation and display occurs in event counter 8 when switch 66 is depressed by the displacement of ramp 68 of diaphragm 70 as depicted in FIG. 13. The event counter 8 will be discussed in further detail below.

Figure 4:
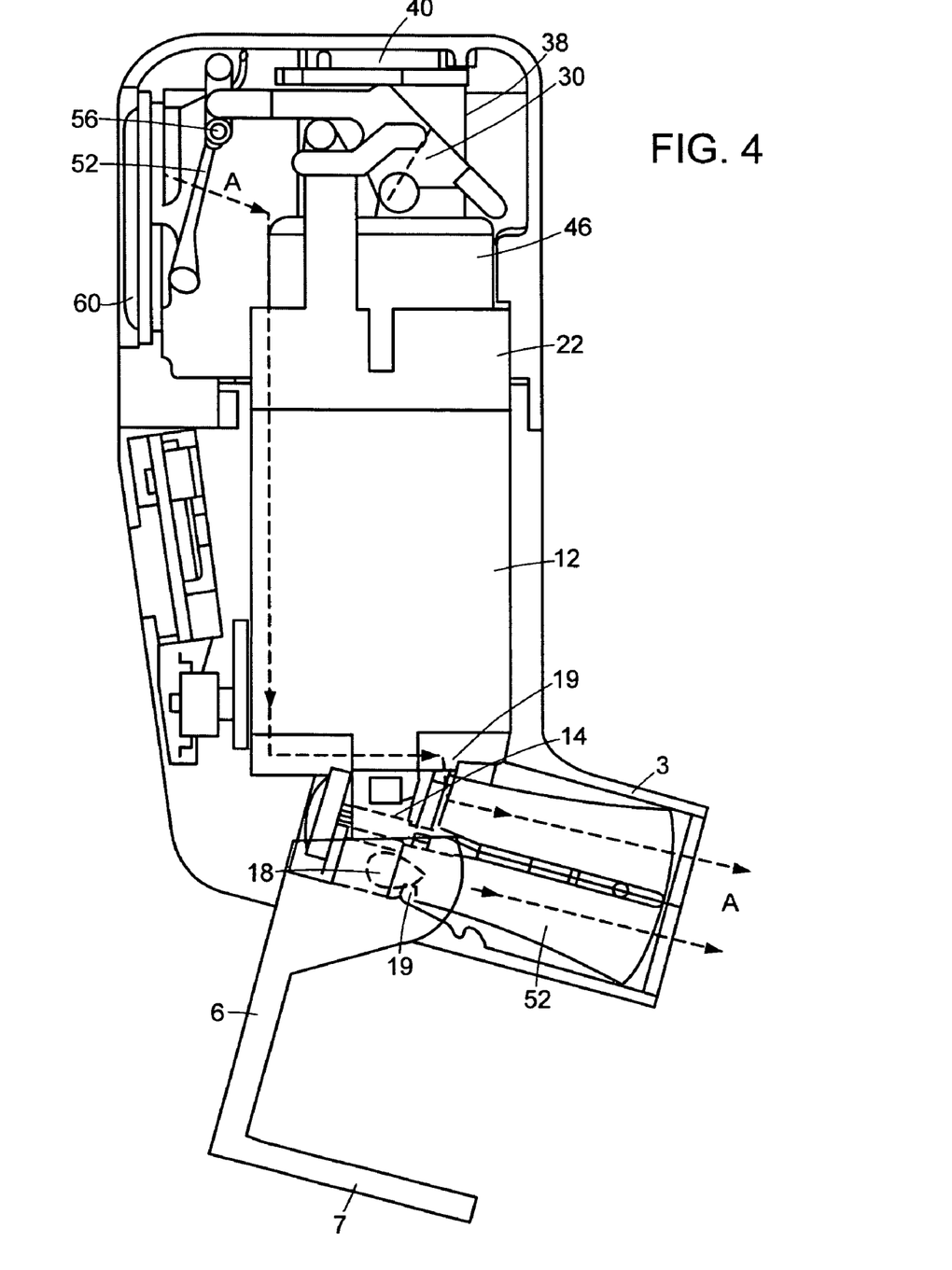

FIG. 4 depicts the breath-actuated inhaler 1 of FIG. 1 in the armed, cocked, and ready to fire state. Cocking arm 6 with mouthpiece cover 7 has been lowered to expose mouthpiece 3 and is now ready for patient inhalation. Cams 18, integral with arm 6 rotate such that the short radius comes into position beneath posts 14 of sleeve 12 allowing sleeve 12 to fall away from the lower end of load sleeve 22. This action permits load sleeve 22 to retract slightly allowing toggle 30 to rotate a few degrees such that cylindrical support bars 57 come to bear on rollers 56 of escapement 52. The breath actuated inhaler 1 is now armed and cocked and ready to fire upon patient inhalation. The inhalation air pathway A-A is directed from openings 19 at the back of vortex nozzle 49 within mouthpiece 3 between canister 46 and sleeve 12 and load sleeve 22 to diaphragm 60. In the pre-fire state, the raised position of load sleeve 22 obstructs vent port 9 in housing structure 100.

Figure 5:
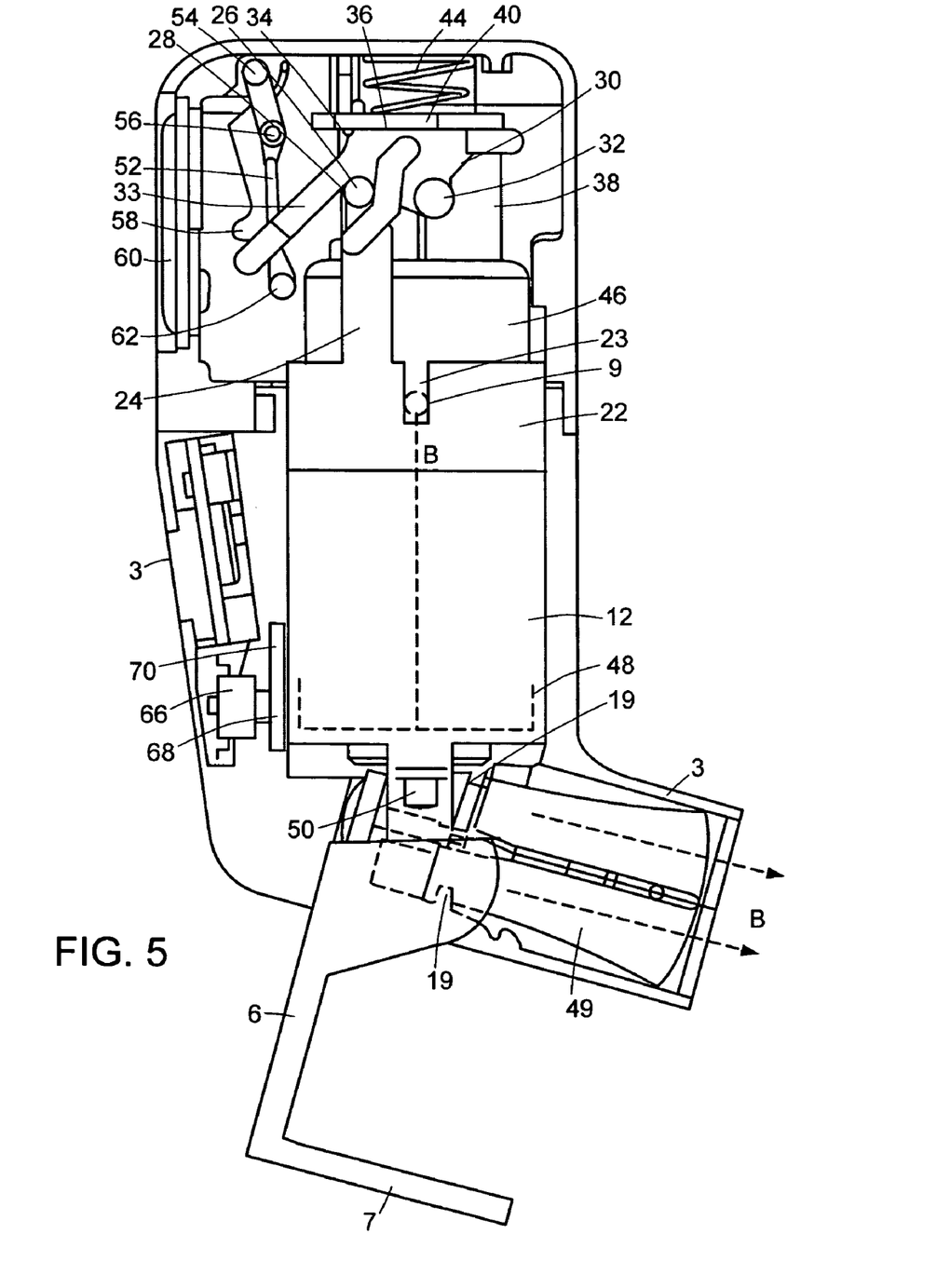

In FIG. 5, the mechanism of the breath-actuated inhaler 1 is in an actuated state. The negative pressure created upon inhalation at mouthpiece 3 is conducted through openings 19 at the rear of vortex nozzle 49 along pathway A-A from FIG. 4, between canister 46 and sleeve 12 and load sleeve 22 to draw diaphragm 60 inward. The displacement of diaphragm 60, bearing upon finger 58 of escapement 52 causes escapement 52 to pivot on post 54, swinging support rollers 56 out from beneath cylindrical bars 57 on platen 33 of toggle 30. A very small displacement of diaphragm 60 is all that is required to impart adequate motion to escapement 52 for rollers 56 to travel "over center" of bars 57 at which point the force of spring 44 further displaces escapement 52. Toggle 30 rotates on axle 32 urged by the downward force of compression spring 44 upon the floor 42 of spring cup 38. Platform 40 slides off of nodes 34 on toggle 30, moves downward, and comes to rest on toggle shelf 36. Integral spring cup body 38, the lower (floor) end of which is in contact with the bottom of canister 46, drives the canister down displacing metering valve stem 50, discharging a dose of drug into vortex nozzle 49. As canister 46 descends, ferrule 48 (shown in dotted line) engages ramp 68 on diaphragm 70 in the wall of lower section 2 depressing switch 66 of event counter 8. The placement and angle of ramp 68 insure that the count is decremented immediately prior to or at drug delivery.

Simultaneous with the displacement of canister 46, the rotation of toggle 30 on axle 32 forces down cylindrical bosses 26 riding in toggle receiver slot 28. Cylindrical bosses 26 transmit the force to load sleeve 22 via arms 24. Motion of load sleeve 22 downward uncovers vent port 9 in housing structure 100, opening make up air route B-B by which an inhalation maneuver post drug delivery may continue. Ambient air entering vent port 9 passes through slot 23, between canister 46 and sleeve 12, to openings 19 in the rear of vortex nozzle 49.

Figure 6:
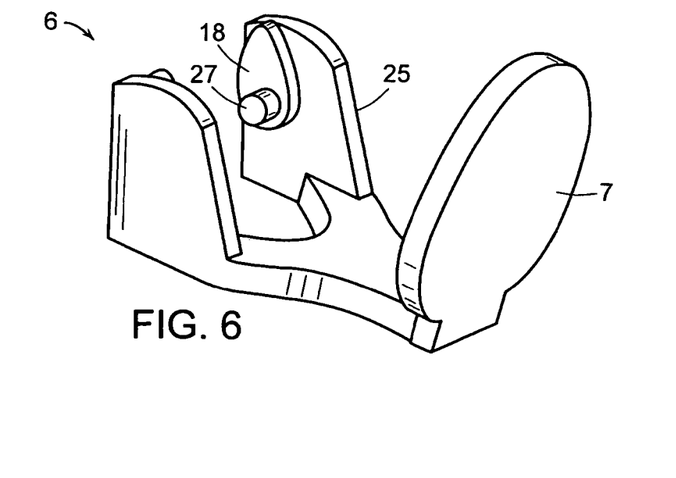
FIG. 6 is a perspective view of the cocking lever with a mouthpiece cover showing the location of the cams for arming and cocking the inhaler.

FIG. 6 depicts the cocking lever 6 with integral mouthpiece cover 7. Cocking lever 6 attaches to the lower section 2 of housing structure 100 by means of posts 27 which are molded integral with cams 18 into the interior surface of side plates 25. Posts 27 snap into openings in lower section 2 of housing structure 100. Rotation of cocking lever 6 raises and lowers sleeve 12 within cylindrical cavity 10.

Figure 7:
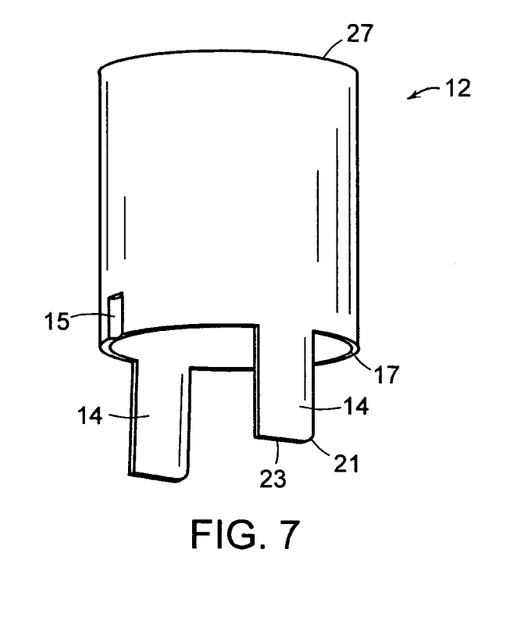
FIG. 7 is a perspective view of a sleeve, which is a component of the arming and cocking system contained within the bottom section of the housing.

As shown in FIG. 7, sleeve 12 has an upper edge 27 that abuts the lower end 29 of load sleeve 22 in the raised, armed, position. Projecting downward from the bottom edge 17 of sleeve 12 are two posts 14 that pass through openings in the bottom of lower section 2 to engage cam lobes 18 on cocking lever 6. Posts 14 are rounded at corners 21 to facilitate engagement with cams 18. Flat regions 23 on the bottom of posts 14 bear on cam lobes 18 during the arming, cocking and firing processes. A slot 15 in the bottom edge 17 of sleeve 12 straddles ramp 68 of diaphragm 70 allowing free access to ferrule 48 on canister 46 for event counter 8 function.

Figure 8:
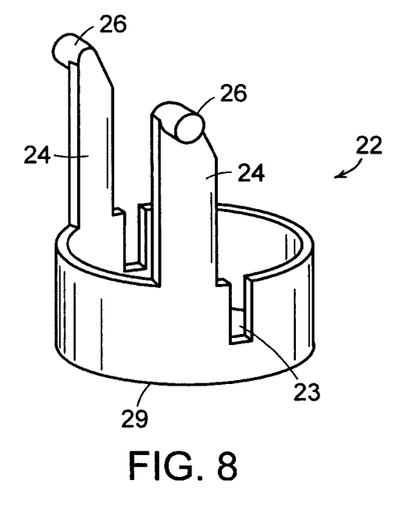
FIG. 8 is a perspective view of the sliding load sleeve showing the detail of the arms and right angle supporting cylinders.

The structure of arms 24 that extend from the upper side of load sleeve 22 is depicted in greater detail in FIG. 8. At the extremities of arms 24 and at right angles thereto are cylindrical bosses 26 that engage slot 28 in toggle 30. Slot 23 in the body of load sleeve 22 opens to the vent port 9 in housing structure 100 between lower section 2 and upper section 4 for makeup air when load sleeve 22 descends within cylindrical cavity 10 upon breath actuation. Therefore, in effect, load sleeve 22 acts as a shuttle valve in performing this function.

Toggle 30 is shown in FIG. 9 and pivots on axle 32 that rides in bearings molded into the top of upper section 4 of housing structure 100. In the armed state, the load force of main spring 44 carried by spring cup 38 is borne on nodes 34 of toggle 30 and the cylindrical bosses 26 on load sleeve 22 act through sleeve 12 with cams 18 of cocking lever 6, to oppose the force of main spring 44. In the ready to fire state, rollers 56 on escapement 52 maintain toggle 30 in the cocked state by supporting cylindrical bars 57 projecting from platen 33. When support at cylindrical bars 57 is removed, toggle 30 rotates on axle 32 urged by main spring 44 forcing spring cup 38 to travel downward coming to rest on shelf 36. The drop from nodes 34 to toggle shelf 36 transfers, via spring cup 38, the force of main spring 44 to canister 46. Spring cup 38 moves within opening 35 in toggle 30. An opening 37 in toggle 30 provides clearance for escapement rollers 56 when toggle 30 rotates, as support at bars 57 slides away. Slot 28 provides translation of the rotation of toggle 30 to a linear travel of load sleeve 22.

Figure 9A:
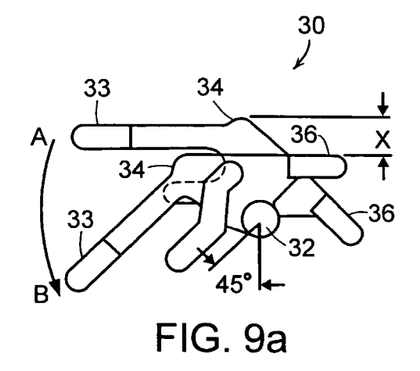
FIG. 9A is a plan view of the toggle shown in FIG. 9.

FIG. 9a, which is a different view of toggle 30, shows the distance that spring cup 38 drops from the node 34 to the shelf 36. This occurs as toggle 30 rotates on axle 32 when rollers 56 of escapement 52 release bars 57 of platen 33 (platen 33 moves from position A to position B). The 45-degree rotation of axle 32, as illustrated, conveys the force of main spring 44 to canister 46. The displacement of canister 46 by a distance X (which is anywhere from 0.125 to 0.150 inches depending on drug canister specifications), is adequate to insure drug delivery.

Escapement 52 is depicted in FIG. 10. Axle 54 of escapement 52 is retained by bearings molded in upper section 4 of housing structure 100. A finger 58 projecting from the front surface of escapement 52 touches the center 59 of diaphragm 60 when the inhaler is at rest or cocked. A spring (not shown) bearing upon the back of escapement 52 biases the escapement 52 toward diaphragm 60. Rail 62 at the lower edge of escapement 52, rests against stop 64 in upper section 4 maintaining the proper angle for rollers 56 to support cylindrical bars 57 on platen 33 of toggle 30 when the inhaler is cocked.

Figure 11:
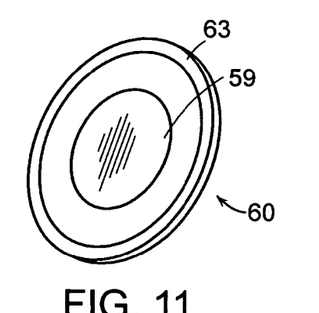
FIG. 11 is a perspective view of the elastomeric diaphragm, which upon inhalation displaces the escapement triggering automatic drug delivery.

As shown in FIG. 1, elastomeric diaphragm 60 has a center 59 that contacts finger 58 of escapement 52. Deflection of diaphragm 60 at inhalation is the breath actuation trigger for the inhaler 1. Diaphragm rim 63 is retained in a channel 61 molded in the wall of upper housing section 4. There are vents 65 in the outside wall of upper section 4 in front of diaphragm 60 to permit unrestrained displacement.

FIG. 12 depicts spring cup 38 that has a lower end surface 42 of cylinder 41 which retains main spring 44 between lower surface 42 and the inside top of upper section 4 of housing 100. The lower end of spring cup 38 bears upon the bottom of canister 46. Nodes 34 and shelf 36 of toggle 30 support top plate 40 from the bottom side. Keyways 43 in plate 40, straddle rails molded into upper housing section 4 preventing rotation of spring cup 38 as it drives canister 46 down when fired.

In FIG. 13 is depicted an event counter switch membrane trigger 70. Membrane trigger 70 is sealed by edge bead 75 within the inner wall 71 of lower housing section 2 as shown in FIG. 3. Membrane trigger 70 is molded of elastomeric material with an external ramp 68 that is deflected by contact with ferrule 48 of canister 46 as the canister 46 descends during firing. The displacement of ramp 68 depresses switch 66 of event counter 8 causing a decrement of one in the display of the doses remaining.

Returning mouthpiece cover 7 to the closed position over mouthpiece 3 after use, rearms the inhaler for the next breath actuation. Rotation of cocking lever 6 (integral with 7) in closing, raises cam lobes 18 into contact with posts 14 on sleeve 12. As sleeve 12 rises, it pushes adjacent load sleeve 22 up in such a manner that cylindrical bosses 26 on arms 24 of load sleeve 22 force toggle 30 to rotate up to the armed, latched, position. Toggle 30 rotates on axle 32 as it is moved upward to a position at which escapement 52, urged by a biasing spring, returns to rest with rail 62 against stop 64. During rotation, toggle 30 also forces spring cup 38 upward, compressing main spring 44 as the bottom edge of 38 shifts from a seat on shelf 36 of toggle 30 to nodes 34. The full, armed, spring force is born by the vertically aligned elements of spring cup 38, toggle 30, sleeve 12 and load sleeve 22, and cams 18. Escapement 52 and diaphragm 60 are effectively decoupled from the inhaler mechanism. This insures against misfire due to accidental impact or other unanticipated events.

As previously discussed, the breath actuated inhaler 1 of the present invention includes an event counter 8. The dispensation history of the event counter 8 can include, but is not limited to, the number of doses of medication or actuations remaining in the canister, the number of actuations of the inhaler during a dosage sequence, the number of doses or actuations taken over a period of time, and the time since the last dispensation of the medication.

Figure 14:
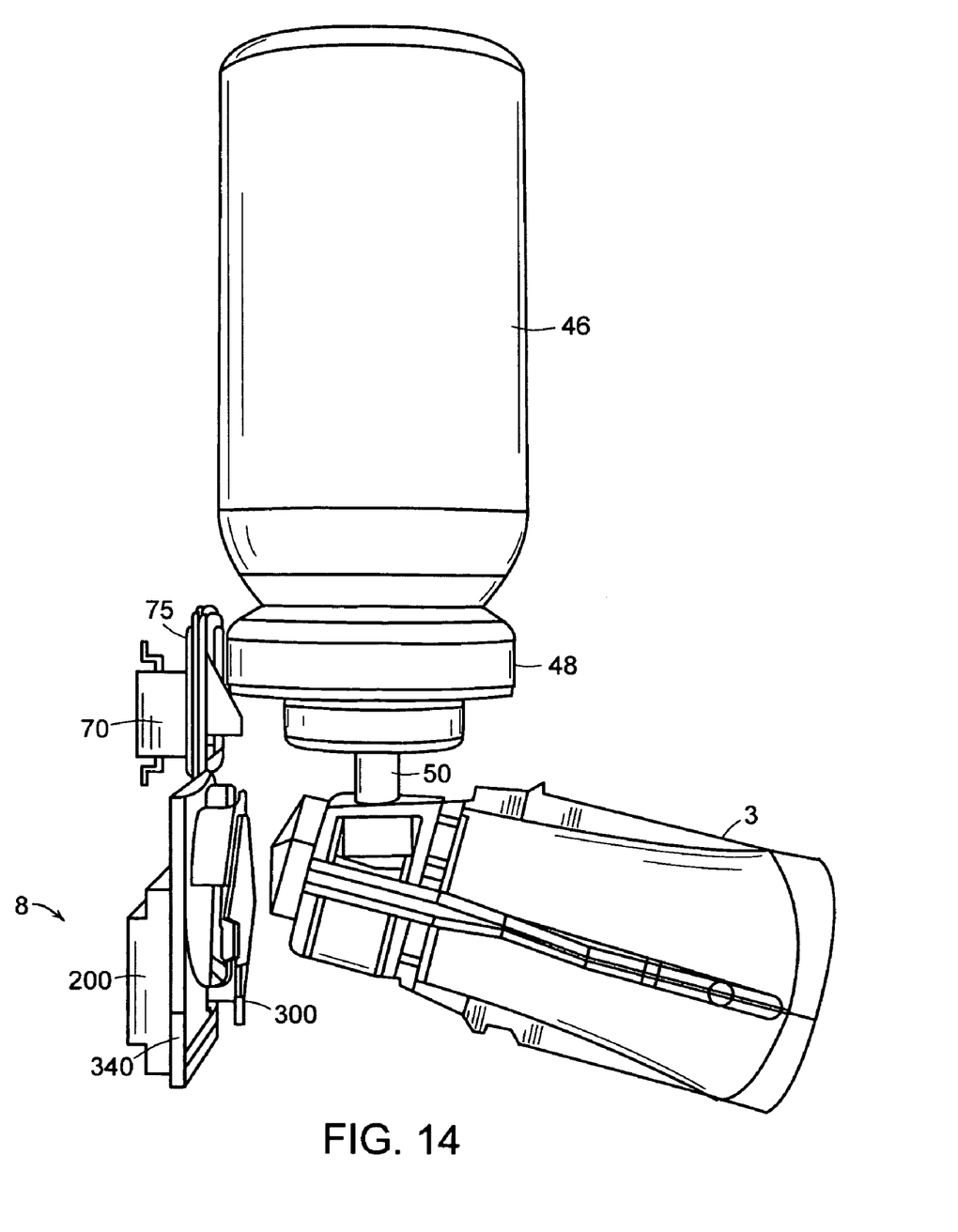
FIG. 14 is an internal plan view of breath actuated inhaler having a dose counter.

Depicted in FIG. 14 is a typical event counter 8 with the display 200 electrically connected thereto. The display 200 is shown physically mounted to the event counter 8, however, other arrangements of the two components may be made. A battery 300 provides the power necessary to operate the event counter 8 and display 200. Also provided as part of the event counter 8 is the event counter switch membrane trigger 70. As shown, the switch membrane trigger 70 is mounted external to a printed circuit board 340 and is isolated from canister 46 and mouthpiece 3 by an elastomeric edge bead seal 75. The switch membrane trigger 70 is electrically connected to circuit board 340, using wires or flexible circuitry (not shown).

The event counter 8 is comprised of a circuit board 340 for mounting all or substantially all of the components of the event counter 8. These components include the battery 300, the display 200, the switch membrane trigger 70, and an application specific integrated circuit (ASIC). The event counter 8 can operate in a variety of counting modes. The manufacturer may select the mode of the apparatus during production. Alternatively, the user may select the mode in an apparatus that is enabled with two or more counting modes.

The breath actuated inhaler 1 of the present invention also includes a vortex nozzle 49 as depicted in FIG. 3 and disclosed in commonly assigned U.S. Pat. No. 6,418,925, the contents of which are expressly incorporated herein by reference. The vortex nozzle 49 is designed to cause the medicament contained within canister 46 to aerosolize when ejected or sprayed into the nozzle. The aerosolization or atomization of the sprayed medicament results in a higher, more uniform dose of medication reaching a patient.

Figure 15:
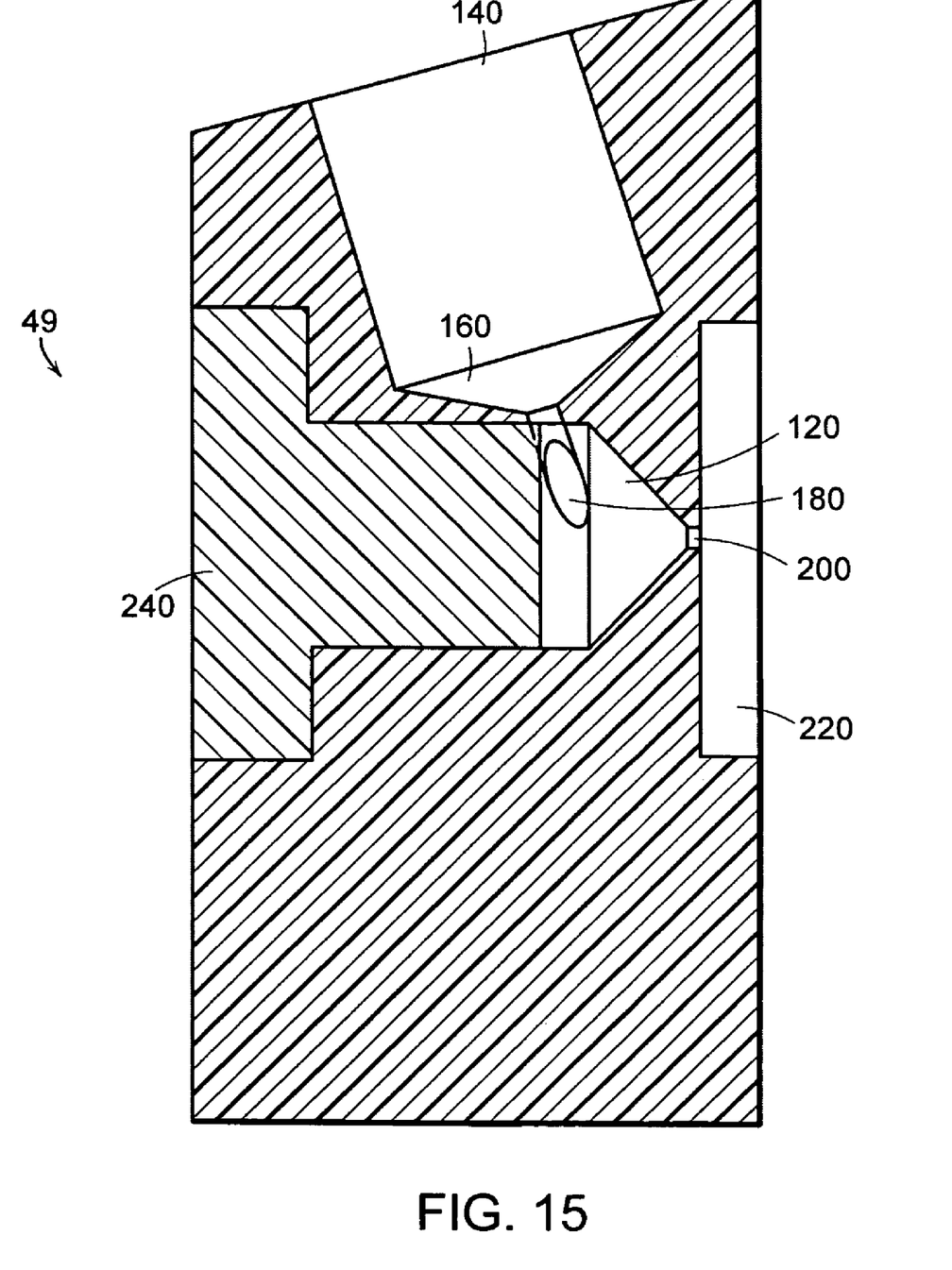
FIG. 15 is a cross-section view of a vortex nozzle design.

FIG. 15 shows a design of vortex nozzle 49. The vortex nozzle 49 works as follows. In nozzle 49 the medicament is fed, under pressure, into a swirl chamber 120 through an inlet 140 into an inlet chamber 160 having an outlet passage 180. The swirl chamber 120 has a first end and a second end where the diameter of the first end is greater than the diameter of the second end. Outlet passage 180 is tangential to the outer circumference of swirl chamber 120. The inlet 140, particularly the outlet passage 180 is set at a specified angle which is 105-degrees from the axis through exit orifice 200 but can be perpendicular to this axis. The liquid entering swirl chamber 120 from outlet passage 180 imparts a high angular velocity creating a low-pressure central region that creates an air-cored vortex. This vortex spins through swirl chamber 120 and emerges with tangential and axial components via an exit orifice 200. Here, a hollow annular spray is produced. This spray exits orifice 200 as a conical sheet through nozzle face 220. The air core in conjunction with the swirl motion creates tremendous shear forces to the exit orifice 200 thereby causing the exiting annular spray to break up into ligaments and drops.

Nozzle face 220 may be flat as shown in FIG. 15 or may have other shapes, such as but not limited to, a conical or parabolic shape. The shape of the nozzle face 220 along with the internal angle of the swirl chamber 120 may be modified to affect the desired retention, plume force, and angle of the resulting plume.

A corresponding nozzle back seal 240 forms the backside of the vortex chamber and is a means for manufacturing the device. Nozzle back seal 24 is inserted into back of the nozzle and extends to the very edge of the tangential passage 180, which feeds liquid into swirl chamber 120. Back seal 240 is preferably attached to the nozzle using ultrasonic welding. In essence, the back surface of the vortex nozzle 46 is flat while the main vortex chamber is shown as primarily funnel shaped with a 90-degree cone leading to the exit orifice 200 but may be modified as aforesaid.

Figure 16:
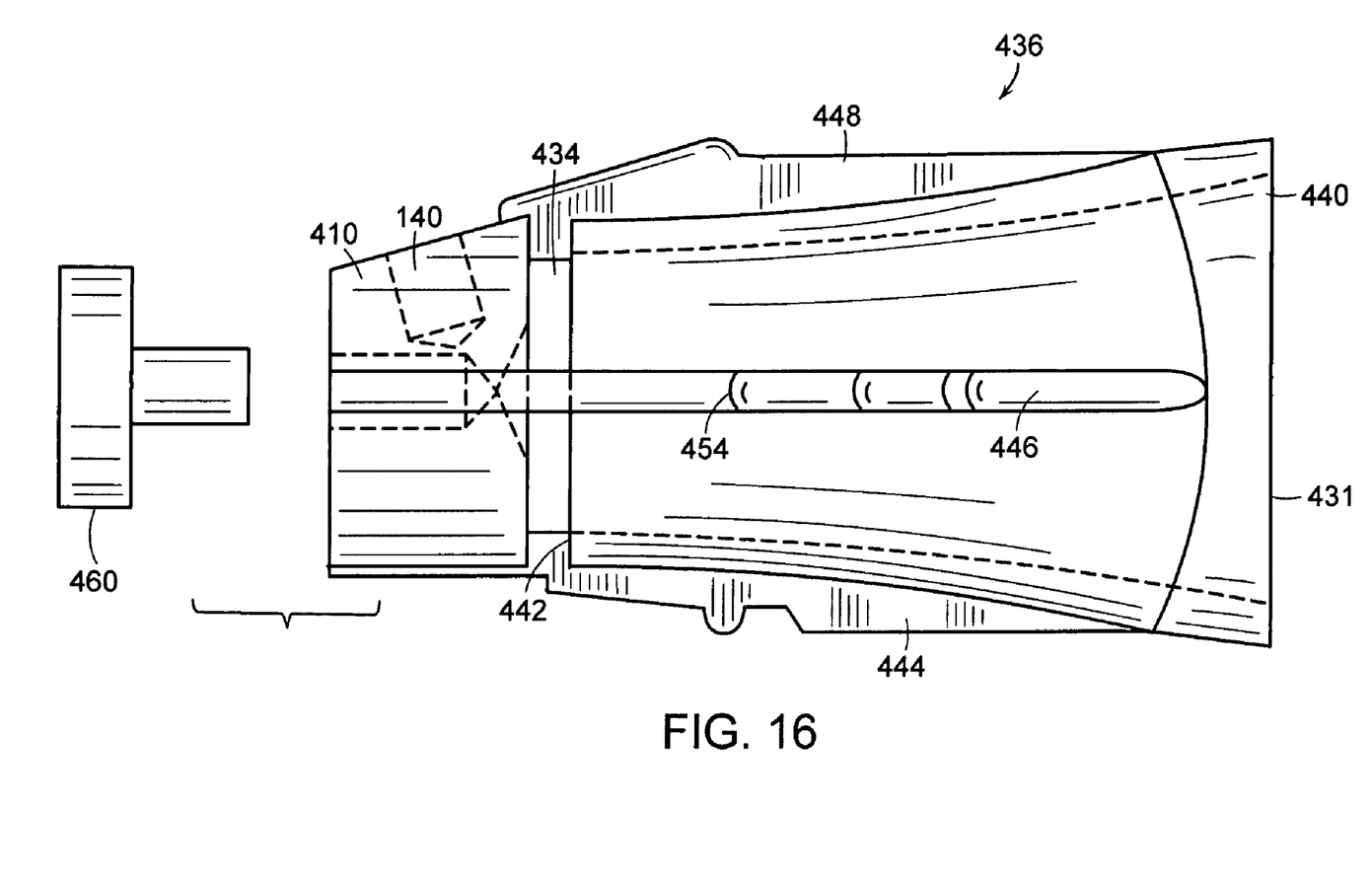
FIG. 16 is a plan view of a vortex nozzle.

FIG. 16 depicts construction of a vortex nozzle where there is shown mouthpiece insert 436, which is intended to be inserted into the mouthpiece 3 of housing structure 100. Insert 436 has a forward or open end 440 and a rearward end 442. Coupled at end 442 is nozzle 410 by way of ribs 444, 446 and 448. Rib 446 has an opposite rib (not shown). Nozzle 410 is positioned at a spaced distance from end 442 so as to create slits 434. A back seal or plug 460 is provided for insertion into the rear of nozzle 410. In this regard, nozzle 410 and insert 436 may be fabricated integrally or separately and then coupled together in an appropriate means suitable for purpose. The material used may be HDPE or any other appropriate material. Plug 460 may be made of a somewhat resilient material as to allow for its insertion into the back of nozzle 410. As can be seen in FIG. 3, upon completion of insertion of insert 436, plug 460 abuts flange 462 on lower section 2 of housing structure 100. This assures plug 460 stops in place and also helps maintain the proper position of inlet 140.

Having described the structure and operation of the breath actuated inhaler 1 of the present invention, the advantages of the inhaler over prior inhalers will now be discussed in detail.

The inhaler of the present invention includes several advantageous structural features. One such feature is the nesting of the main spring within the toggle mechanism. To implement this feature, the release arm was "de-coupled"

from the toggle and pivotally attached to the upper unit of the housing, where its motion during actuation does not move it into the space occupied by the main spring. This allows for the use of a main spring of increased diameter, thereby increasing the actuation force capacity of the device.

Another advantageous feature is the interfacing of the diaphragm and release mechanism within a very small space. That is, the toggle is designed to pass over the moving escapement, within the same space envelope, without interference. Such "nesting action" reduces the space occupied by the release mechanism. Nevertheless, the escapement still has access outside the "travel envelope" for interfacing with the diaphragm and travel stops on the housing.

Still another advantageous feature is the interfacing of the sleeves with the release mechanism. In particular, the two cylindrical bosses on the upper sleeve fit into mating slots on the toggle, causing the upper sleeve to move vertically in response to the pivoting motion of the toggle. Upon closure of the mouthpiece cover, the upper sleeve pivots the toggle to its closed position, compressing the main spring and resetting the device.

Yet another advantageous feature of the device is that of using a "sleeve valve" to open a make-up air pathway. More specifically, the openings in the upper sleeve provide the make-up air pathway. When the device fires, the toggle rotates downward, urging the upper sleeve downward. When the upper sleeve reaches the lower limit of travel, the two openings in the sleeve align with ports in the upper housing unit. The alignment of the holes creates an open pathway to ambient air outside the device, allowing it to be drawn through the device as "make-up" air for inhalation. The size and shape of the openings on the upper sleeve, and/or the ports in the upper housing unit, may be tailored to manage inhalation resistance and flow rate.

An additional advantage of the device of the present invention is that the bayonet twist lock joining the upper and lower parts of the assembly provide for easy disassembly for cleaning of the nozzle orifice and, in the event of mechanical failure, operation as a conventional "press and breathe" device.

An additional advantage is the means by which the event counter is affixed to the inhaler. The counter is totally isolated from the airflow path and all other components by a membrane/ramp switch seal in the wall of the inhaler body. This feature also prevents moisture from reaching the event counter during rinsing or washing of the drug delivery nozzle.

Still another advantageous feature is the way the event counter is integrated into the device, particularly the interfacing of the event counter with the ferrule of the canister. Access to the ferrule is facilitated by the location of the release mechanism and triggering function above the canister, leaving the entire lower portion of the canister and metering valve open to access.

The present inhaler uses a mechanical (non-vacuum) release mechanism that is located at the top of the device, above the canister. This approach provides for ample stored energy capacity, while avoiding the issues associated with a mechanism that "surrounds" the metering valve. In particular, it is noted that there are no small parts or features in the inhalation air pathway; the canister ferrule is accessible to an isolated event counter via a membrane/ramp interface; and the layout does not require compromise of any kind in the design of the vortex nozzle.

The present inhaler uses a flexible diaphragm for triggering, instead of a rotating vane/door. A diaphragm is much easier to locate away from the inhalation airflow path, facilitating the placement of the release mechanism at the top of the device. There are two significant advantages to this arrangement, first the mechanism does not encroach upon the airflow pathway and second, there is no way components can be inhaled in the event of mechanical failure. Further, in as much as the present inhaler does not employ a vacuum "holdup" mechanism to retain stored energy in the spring, the overall force capacity of the inhaler is sufficient to actuate any metering valve commonly used in pressurized metered dose inhalers (pMDIs).

The present inhaler uses sliding sleeves to link the mouthpiece cover to the arming mechanism. Thereby, allowing the actions of opening and closing the mouthpiece cover to be used to input energy to arm the device (no separate arming lever is needed). The sleeves (upper and lower) also serve as an interface between the detachable upper and lower units of the device. In the rest state (mouthpiece-cover-closed), the force of the compressed main spring is resisted by the sleeves and the mouthpiece cover, which is closed past an actuation point. Importantly, the release mechanism components—physically smaller than prior release mechanism components—are not loaded in this state. Therefore, motion-induced misfires are unlikely.

The advantages of the present invention stand in contrast to some of the disadvantages of prior breath actuated inhalers. The disadvantages of one type of prior breath actuated inhalers include: (1) small parts and/or features in the inhalation air pathway, allowing for the possibility of a user inhaling a mechanical component of a failed device; (2) susceptibility to inadvertent triggering; (3) triggering mechanisms that effectively prevent access to the ferrule of the canister, which is a very desirable area from which to activate a counter mechanism (FDA guidance currently recommends a counter on all new devices); (4) a triggering vane located in the mouthpiece and hinged very close to the nozzle orifice, acting as a "ceiling" just above the orifice during delivery of the dose potentially compromising spray quality and metrics of the emitted dose, (5) the use of a lever to arm the device, requiring added parts and an additional user operational step and; (6) components of the device do not separate enabling the patient to use the device as a conventional "press and breathe" inhaler in the event of mechanical failure.

The disadvantages of another type of prior breath actuated inhalers include: (1) the use of a "vacuum-holdup" mechanism that retains stored energy in the compressed spring, limiting the stored energy capacity of the device according to the ambient air pressure, the volume of the device and the integrity of the vacuum seals—for this reason the device does not have enough stored energy capacity to actuate all metering valves, significantly limiting the device's applicability; (2) preloading of the metering valve, that is maintaining the medicament canister in a state in which the valve stem is partially depressed, can have undesirable side effects, such as allowing for gradual leaking of drug or propellant; and (3) dependence on the creation of a consistently reproducible vacuum seal can adversely affect reliability and manufacturing yield of the device.

Modifications to the present invention would be obvious to those of ordinary skill in the art in view of this disclosure, but would not bring the invention so modified beyond the scope of the appended claims.

What is claimed is:

1. A breath actuated metered dose inhaler, comprising:
   a housing;
   a mouthpiece positioned at one end of the housing;

a mechanical release mechanism positioned at another end of the housing, wherein said release mechanism comprises a spring that is compressed to store energy for the purpose of providing the metered dose; and wherein said release mechanism further comprises a rocker, wherein the spring is nested within a spring cup that engages an outer surface of the rocker, said rocker which is operable to pivot to allow compression and decompression of the spring;

whereby the release mechanism is triggered by a diaphragm and the air inhalation pathway is unimpeded by the release mechanism.

2. A breath actuated metered dose inhaler as recited in claim 1, wherein the release mechanism further comprises a release arm for impeding the rocker prior to triggering of the inhaler.

3. A breath actuated metered dose inhaler as recited in claim 2, wherein the rocker does not bear on the release arm in a rest state and does bear on the release arm in a ready-to-fire state.

4. A breath actuated metered dose inhaler as recited in claim 2, wherein the inhaler is triggered upon movement on the release arm by the diaphragm.

5. A breath actuated metered dose inhaler as recited in claim 1, further comprising a mouthpiece cover and a sleeve, wherein the sleeve contacts the mouthpiece cover and the rocker, and wherein the rocker is pivoted to compress the spring in response to movement of the sleeve which is caused by movement of the mouthpiece cover.

6. A breath actuated metered dose inhaler as recited in claim 5, wherein the sleeve includes slots for allowing make-up air to enter the housing.

7. A breath actuated metered dose inhaler as recited in claim 1, further comprising a mouthpiece cover, a lower sleeve and an upper sleeve, wherein the lower sleeve contacts the mouthpiece cover and the upper sleeve contacts the lower sleeve and the rocker, and wherein the rocker is pivoted to compress the spring in response to movement of the upper sleeve which is caused by movement of the lower sleeve produced by movement of the mouthpiece cover.

8. A breath actuated metered dose inhaler as recited in claim 7, wherein the upper sleeve includes slots for allowing make-up air to enter the housing.

9. A breath actuated metered dose inhaler as recited in claim 1, further comprising an event counter for indicating the number of doses remaining in the inhaler as well as the number of doses taken during a dose sequence.

10. A breath actuated metered dose inhaler as recited in claim 1, wherein the housing comprises a separable upper and lower section thereby allowing for manual press and breath operation to facilitate priming or to use in the in the event of release mechanism failure.

11. A breath actuated metered dose inhaler comprising:
a housing:
a mouthpiece positioned at one end of the housing; and
a mechanical release mechanism positioned at another end of the housing, whereby the release mechanism is triggered by a diaphragm and the air inhalation pathway is unimpeded by the release mechanism; and
wherein said release machanism comprises a spring that is compressed to store energy for the purpose of providing the metered dose; and wherein said release mechanism further comprises a rocker, wherein the spring is nested within a spring cup that engages an outer surface of the rocker, said rocker which is operable to pivot to allow compression and decompression of the spring; and
a vortex nozzle positioned within the mouthpiece, wherein said nozzle comprises a nozzle housing including an inlet which opens into a swirl chamber having an outer circumference, a diameter and a first swirl chamber end having a diameter, the inlet being tangential to the outer circumference and set at an angle to the first swirl chamber end, an exit passage positioned at a second swirl chamber end having a diameter, the diameter of the first swirl chamber end having a diameter greater than the diameter of the second swirl chamber end, the exit passage communicating with a nozzle face through which an aerosol is discharged.

12. A breath actuated metered dose inhaler as recited in claim 11, wherein the nozzle face is flat.

13. A breath actuated metered dose inhaler as recited in claim 11, wherein the nozzle face has a conical shaped.

14. A breath actuated metered dose inhaler as recited in claim 11, wherein the nozzle face has a parabolic shape.

15. A breath actuated metered dose inhaler as recited in claim 11 further comprising an event counter for indicating the number of doses remaining in the inhaler as well as the number of doses taken during a dose sequence.

16. A breath actuated metered dose inhaler as recited in claim 11 wherein the event counter comprises:
a display;
a battery to provide power necessary to operate the dose counter;
an event counter switch trigger; and
a printed circuit board for mounting all or substantially all of the said dose counter components.

* * * * *

UNITED STATES PATENT AND TRADEMARK OFFICE
CERTIFICATE OF CORRECTION

PATENT NO. : 7,219,664 B2
APPLICATION NO. : 10/908133
DATED : May 22, 2007
INVENTOR(S) : Tom Ruckdeschel et al.

It is certified that error appears in the above-identified patent and that said Letters Patent is hereby corrected as shown below:

Column 7, line 14, "after use, rearms" to read as --after use rearms--

Column 7, line 16, "in closing, raises cam lobes" to read as --in closing raises cam lobes--

Column 9, line 33, "housing unit, may be" to read as --housing unit may be--

Column 11, line 8, Claim 1: "which is operable to pivot" to read as --being operable to pivot--

Column 11, line 22, Claim 4: "upon movement on the release arm" to read as --upon movement of the release arm--

Column 11, line 49, Claim 10: "a separable upper and lower section" to read as --separable upper and lower sections--

Column 12, line 2, Claim 10: "or to use in the in the event" to read as --or to use in the event--

Column 12, line 11, Claim 11: "release machanism comprises" to read as --release mechanism comprises--

Column 12, line 16, Claim 11: "which is operable to pivot" to read as --being operable to pivot--

Column 12, line 33, Claim 13: "has a conical shaped." to read as --has a conical shape.--

Column 12, line 40, Claim 16: "as recited in claim 11" to read as --as recited in claim 15--

Signed and Sealed this

Twentieth Day of July, 2010

David J. Kappos
*Director of the United States Patent and Trademark Office*